United States Patent [19]

Sowerby

[11] 4,314,155

[45] Feb. 2, 1982

[54] METHOD AND APPARATUS FOR ELEMENTAL ANALYSIS EMPLOYING COMBINATION OF NEUTRON INELASTIC SCATTERING AND γ RAY SCATTERING

[75] Inventor: Brian D. Sowerby, Kareela, Australia

[73] Assignee: Australian Atomic Energy Commission, Coogee, Australia

[21] Appl. No.: 59,003

[22] Filed: Jul. 19, 1979

[51] Int. Cl.³ .................. G01V 5/00; G01N 23/00
[52] U.S. Cl. .................. 250/253; 250/255; 250/358 R; 250/390
[58] Field of Search .............. 250/358 R, 255, 259, 250/260, 253, 270, 265, 390

[56] References Cited

U.S. PATENT DOCUMENTS

| | | | |
|---|---|---|---|
| 2,644,891 | 7/1953 | Herzog | 250/270 |
| 2,785,314 | 3/1957 | Grahame | 250/265 |
| 3,780,301 | 12/1973 | Smith et al. | 250/270 |
| 3,849,646 | 11/1974 | McKinlay et al. | 250/270 |

*Primary Examiner*—Alfred E. Smith
*Assistant Examiner*—Carolyn E. Fields
*Attorney, Agent, or Firm*—Ladas & Parry

[57] ABSTRACT

The present invention discloses a method and apparatus of elemental analysis which finds particular application in the on-line analyses of the specific energy (calorific value) of coal or coke by the determination of carbon content. Analysis is achieved by a comparison of the output of neutron inelastic scatter which produces first γ rays and of scatter of second γ rays. Preferably 4.43 MeV carbon γ rays are used and, in addition, one or more of moisture, ash, or hydrogen content of coal or coke can be measured using 2.2 MeV hydrogen capture γ rays. The method and apparatus have the advantage of providing a compensated count rate that is essentially independent of sample compaction.

14 Claims, 7 Drawing Figures

METHOD AND APPARATUS FOR ELEMENTAL ANALYSIS EMPLOYING COMBINATION OF NEUTRON INELASTIC SCATTERING AND γ RAY SCATTERING

The present invention provides an improved method and apparatus for elemental analysis as described based on the measurement of γ rays from neutron inelastic scattering combined with a γ ray scattering measurement on essentially the same sample volume. The γ ray scattering measurement acts as a correction to the neutron inelastic scattering measurement for variables such as sample bulk density, bulk density gradients and sample thickness. The matching of the two gauges enables a higher accuracy to be obtained than has been previously achieved. This is particularly important in the on-line analysis of the specific energy (formerly calorific value) of coal for which the carbon content needs to be determined to relative accuracy of better than 1%. Previous attempts to analyse carbon in bulk coal samples have not achieved this accuracy.

When a rock or mineral product is bombarded with fast neutrons, there are a number of competing processes of γ ray excitation as outlined in Table 1.

TABLE 1

Processes by which energetic neutrons interact with matter to produce γ rays

| Process | Symbol | Description |
|---|---|---|
| Inelastic | X(n,n′γ)X | A nucleus is excited to one of its higher states by a neutron which loses a corresponding amount of energy. The nucleus returns to its ground state by promptly emitting γ radiation. |
| Radiative | X(n,γ)Y | A nucleus undergoes transmutation by capturing a thermal neutron. The product nucleus promptly de-excites with the emission of γ rays. |
| Activation | | An unstable nucleus is formed by neutron capture and in the decay of this product nucleus, delayed γ rays are emitted. The intensity of the delayed γ rays varies at a rate dependent on the half life of the product nucleus. |

In the neutron inelastic scattering process, a nucleus is excited to one of its higher states by a neutron of incident energy greater than the energy of this higher state. γ rays are emitted promptly from this state, usually in less than $10^{-10}$ sec as determined by the lifetime of the state. Neutron inelastic scattering is suited to the analysis of light elements some of which, such as carbon, are not readily accessible by other bulk analysis methods. Cross sections for the production of inelastic scattered γ rays from some elements are listed in Table 2.

TABLE 2

Approximate cross sections for prominent γ rays from neutron inelastic scattering on a number of elements.

| Element | γ Ray Energy (MeV) | Production Cross Section (mb) at neutron energy $E_n$(MeV) in brackets | |
|---|---|---|---|
| Carbon | 4,43 | 350 | ($E_n$ = 6,5) |
| Oxygen | 6,13 | 100 | ($E_n$ = 7,1) |
| Fluorine | 0,20 | 530 | ($E_n$ = 2,6) |
| Sodium | 0,44 | 700 | ($E_n$ = 2,6) |
| Magnesium | 1,37 | 700 | ($E_n$ = 4,0) |
| Aluminum | 0,84 | 102 | |

TABLE 2-continued

Approximate cross sections for prominent γ rays from neutron inelastic scattering on a number of elements.

| Element | γ Ray Energy (MeV) | Production Cross Section (mb) at neutron energy $E_n$(MeV) in brackets | |
|---|---|---|---|
| | 1,01 | 250 | ($E_n$ = 3,0) |
| Silicon | 1,78 | 700 | ($E_n$ = 4,0) |
| Iron | 0,85 | 860 | ($E_n$ = 2,6) |

A number of workers have studied γ ray spectra from neutron inelastic scattering to assess the potential of the technique for elemental analysis. Elements examined include many of the common lighter elements. These studies are reported in Anal. Chim. Acta 53 (1971) 401 (Allan et al.); UCRL-14654, Rev. 1 (1968) (Waggoner et al.); TID-20080 (1963) (Martin et al.); Radiochemical Methods of Analysis (Proc. Symp. Salzburg 1964) 1 IAEA Vienna (1965) (Christell et al.); J. Radioanal. Chem. 4 (1970) 305 (Pierce et al.); and J. Radional. Chem. 10 (1972) 83 (Pierce et al.). However, most of this work has been a preliminary nature only. None of these workers used γ ray source measurements to compensate for sample density and geometry effects and errors quoted were in excess of 5% relative.

Probably the largest project on the application of neutron inelastic scattering to analysis was undertaken by Texas Nuclear Corporation. Texas Nuclear built a pilot plant facility for the analysis of bulk materials on a conveyor belt, as described by Parker et al. Mater. Eval. 25, (1967), 214. The application of nuclear techniques to the analysis of carbon, oxygen, silicon and aluminium in coal was studied using a 14 MeV neutron generator. Carbon and oxygen were measured by fast neutron inelastic scatter and silicon and aluminium by fast neutron activation. Neutron-induced γ ray measurements were made on bulk coal samples of constant physical dimensions and no measurements were made using a γ ray source. The outcome of this work is summarised by Berry and Martin in Adv. Activ. Analysis 2, (1972), 89 as follows:

"The analyses for Si and Al were successfully demonstrated but the measurements of C and O were not sufficiently encouraging for process control. Oxygen could perhaps have been more accurately measured by activation and delayed γ ray counting, but the belt speed was not rapid enough for this measurement to be made. The difficulty with carbon was that neither the sensitivity nor the accuracy was sufficient for meaningful determination of the calorific value of coal. To achieve the desired accuracy in the carbon determination (better than 0.5% C), sophisticated instrumentation, in the form of a pulsed neutron source and a gated time-of-flight spectrometer, is required (Martin, Mathur and Morgan, TID-20080, 1963). This type of instrumentation was considered too elaborate and expensive at that time to justify further work on coal."

Also, in discussing the same work, Rhodes et al. in ORO-2980-18 (1968) stated that:

"Results with stationary coal indicated that the whole system functioned satisfactorily and that measurable signals were obtainable for the four elements (carbon, oxyen, aluminium and silicon) . . . Neutron inelastic scattering results were not obtained with moving samples. The main problem in this case was the low signal to background ratio for the 4.43 MeV carbon peak, as is seen in FIG. 10. It was considered that under these circumstances the required 18% accuracy on carbon content was not achievable."

Stewart, in Instrument Soc. Amer. Trans. 6, (1967), 200 has reported laboratory neutron inelastic scattering measurements for carbon on static samples of fly ash (2.7 to 16.4 wt % C) and iron ore sinter mix (6.2 to 8.6 wt % C). Using annular geometries and no γ ray scattering compensation measurements, Stewart reported an accuracy of 0.5 wt % C, equivalent to a relative accuracy of 7%.

Christell and Ljunggren in Proc. Symp. Salzburg (1964) 1, IAEA Vienna, (1965), 263 have studied the analysis of iron in iron ore using capture γ rays and inelastic scattering γ rays. Measurements were performed in the laboratory on samples of dimensions 300×200×30 mm thick which had been vibrated for 3 minutes to minimise bulk density variations. Accuracies of approximately ±10% relative were obtained.

In its broadest form, the apparatus, of the present invention, for quantitatively measuring the concentration of an element in a sample comprises a neutron inelastic scatter assembly, a γ ray scatter assembly and means to calculate said concentration from the inputs of said assemblies, said assemblies being matched to measure over essentially the same volume of said sample, said neutron inelastic scatter assembly comprising a first source yielding neutrons having energy sufficient to produce inelastically scattered first γ rays from a stable isotope of said element, a first detector to detect said first γ rays, and first shield means associated therewith to reduce the intensity of direct source γ rays, said γ ray scatter assembly comprising a second source yielding second γ rays, a second detector to detect said second γ rays scattered from said sample, and second shield means associated therewith to reduce the intensity of direct source γ rays. The matching is required to properly correct for density variations and inhomogeneities in the samples being measured.

The invention also provides a method for quantitatively measuring one or more elements in a sample, said method comprising combining the results of (i) a measurement of neutron inelastic scatter γ rays over a selected volume of said sample, and (ii) a measurement of γ ray scatter over said selected volume.

Measurements from the γ ray scattering assembly are used as a correction to the neutron inelastic scattering measurements. The first shield serves to reduce the intensity of direct source γ rays and neutrons at the detector. The second shield serves to reduce the detected intensity of direct γ rays from the source of second γ rays. The sources, detectors and shields of both the neutron inelastic scattering assembly and the γ ray scattering assembly may conveniently be located on the same side of the sample being measured. Alternatively, the detectors for both the neutron inelastic scatter assembly and the γ ray scatter assembly can be located on the opposite side of the sample to their sources detecting γ rays scattered, transmitted or produced by the sample. In this case the shield means between the sources and detectors can be placed on either side of the sample.

In an alternate embodiment of the invention both assemblies may be incorporated into one unit wherein measurements are made by interchanging the neutron and γ ray sources.

In yet a further embodiment of the invention a composite neutron/γ ray source may be employed with one detector. In this embodiment the γ rays from neutron inelastic scatter and γ ray scatter would be separated by pulse-height analysis.

In analysing materials having a variable moisture content it may be necessary to apply a correction. In this case a correction may be applied by measuring the intensity of 2.2 MeV hydrogen capture γ rays, or, the thermal or epithermal neutron flux either in the neutron inelastic scatter assembly or in a separate assembly. Other suitable measurements would be capacitance or infra-red reflectance.

In a backscatter γ assembly the single scattering output, P, can be expressed as follows:

$$P \propto \sum_X \sum_Y \sum_Z N P_1 P_2 P_3 \qquad (1)$$

where

X, Y, Z = cartesian coordinates

N = number of electrons in volume element $\Delta v$, $P_1$ = probability that γ ray will reach $\Delta v$, $P_2$ = probability that γ ray scattered in direction of detector, $P_3$ = probability that scattered γ ray reaches the detector.

The terms $P_1$ and $P_3$ are of the form $1/R^2 \exp(-\mu x)$ where R is the distance from the source (or detector) to $\Delta v$, $\mu$ the γ ray absorption coefficient and x the distance the γ ray must travel through the sample. The geometry dependent term in the assembly response is therefore roughly proportional to $P_1 \cdot P_3$ which is equal to $(1/R_i^2 R_o^2) \cdot \exp(-\mu_i x_i - \mu_o x_o)$ where the subscripts i and o refer to the incoming and outgoing radiations respectively. A similar result holds for the neutron inelastic scattering gauge.

For constant source to detector distance and increased source to sample distances, the relative effect of the $(1/R_i^2 R_o^2)$ term is reduced and sample penetration is effectively increased. In this way the penetration depths of the neutron and γ assemblies can be effectively matched. As the radiation penetration is usually greater for the neutron assembly, the source to sample distance for this assembly is smaller than for the γ backscatter assembly.

The application of the method is not restricted to the use of the two separate backscatter gauges as described above. However, this geometry is favourable as matching of the gauge responses is relatively simple and the geometry is suitable for on-line conveyor belt analysis. If required, depth penetration of the backscatter gauges can be increased by collimating the neutron and/or γ ray beams. Matching can also be improved by a number of alternative means including (i) varying the thickness of shielding through which scattered γ rays have to pass before reaching the detector on the γ assembly to preferentially select singly or multiply scattered γ rays; (ii) reducing the source-to-detector separation on the γ assembly compared to the neutron assembly.

The preferred embodiments of the invention are described with reference to the accompanying drawings in which.

Figure 1:
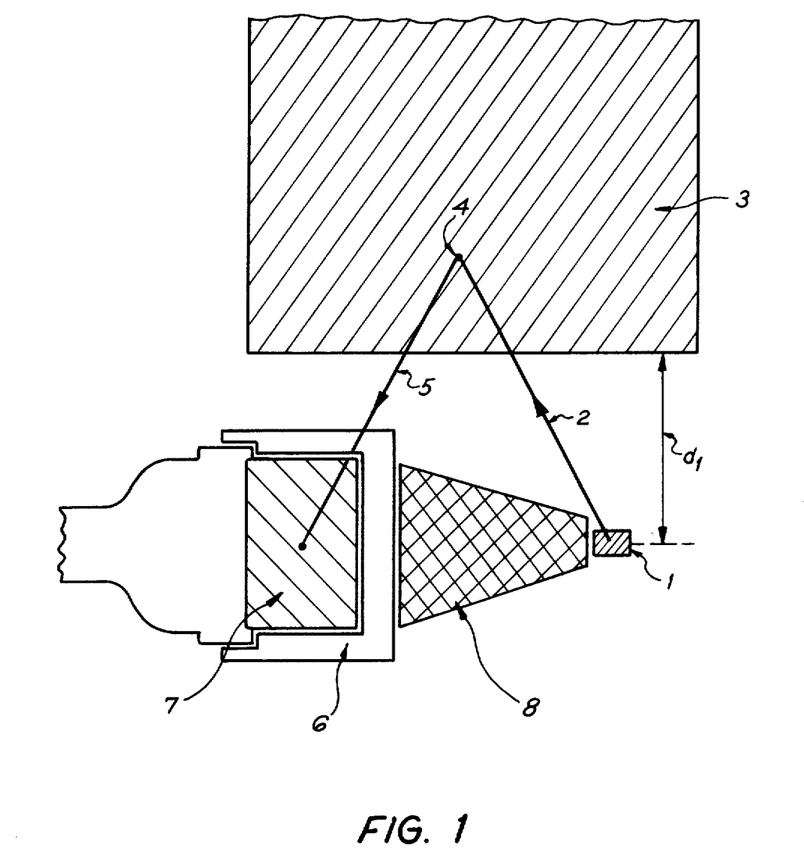
FIG. 1 is a cross sectional view of the assembly used in the determination in coal using neutron inelastic scattering.

In the neutron inelastic scattering assembly depicted in FIG. 1, a neutron source 1 (e.g. $^{238}$Pu-Be) emits neutrons which follow a path such as 2 into a sample 3 (e.g. a coal sample) where they strike atoms of the element being determined at 4 thereby producing $\gamma$ rays which follow a path such as 5 through a neutron shield 6 to a detector 7 which is shielded from the neutron source 1 by a further shield 8. The neutron source 1 is spaced from the sample 3 by a distance $d_1$. A suitable shield 6 is boron trioxide which shields the detector 7 from scattered neutrons whereas tungsten, lead or bismuth would be suitable as shield 8 to shield the detector 7 from the source 1. A suitable detector 7 would be a 150 mm diameter $\times$ 100 mm thick NaI(Tl) crystal. 165 mm would be suitable as distance $d_1$.

Figure 2:
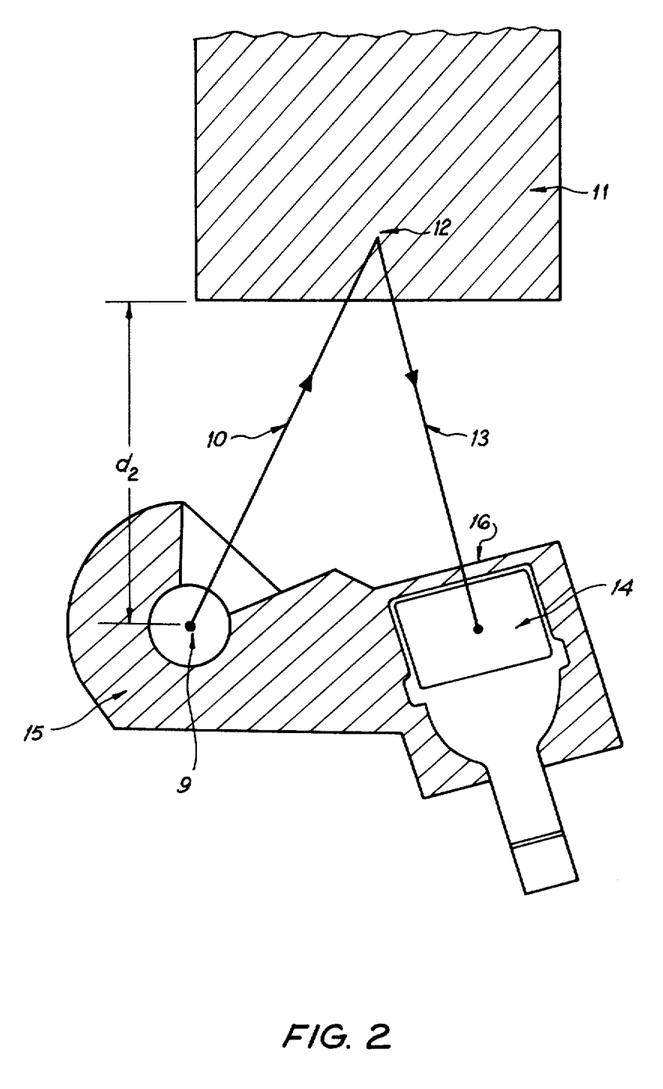
FIG. 2 is a cross sectional view of the γ ray back-scatter assembly, the output of which is used to correct the neutron inelastic scattering measurement (FIG. 1)

In the $\gamma$ ray backscatter assembly depicted in FIG. 2, a $\gamma$ source 9 (e.g. 120 mCi $^{60}$Co) emits $\gamma$ rays which follow a path such as 10 into a sample 11 (e.g. a coal sample) where they strike atoms of the element being determined at 12 thereby producing scattered $\gamma$ rays which follow a path such as 13 to detector 14. The detector 14 is shielded from $\gamma$ radiation by shield 15 which is of reduced thickness at 16 to permit penetration of a proportion of scattered $\gamma$ rays following paths such as 13 to reach the detector 14. The detector 14 is shielded from the source 9 by means of shield 15. The source 9 is spaced from the sample 11 by distance $d_2$. Lead is suitable as shield 15. The detector 7 described for the neutron inelastic scattering assembly would be suitable as detector 14. 350 mm would be a suitable distance $d_2$.

The method was tested by measuring the carbon content of coal samples using the experimental assemblies shown in FIGS. 1 and 2. Boron trioxide was chosen for the thermal neutron shield as it does not contain carbon or hydrogen. Alternative neutron shields include lithium metal, lithium compounds and other boron compounds.

The neutron source used was a $^{238}$Pu-Be source of output $2 \times 10^7$ neutrons/sec. In practice any neutron source which yields neutrons of energy above the inelastic scattering threshold could be used. Suitable neutron sources for inelastic scattering analysis (although not necessarily carbon analysis) include the various $\alpha$-emitter Be mixtures, $^{252}$Cf and neutron generators (tritium-deuterium or deuterium-deuterium). The $\gamma$ source used in FIG. 2 was 120 mCi $^{60}$Co. Any $\gamma$ ray source which yields $\gamma$ rays of energy suitable to allow matching of the neutron and $\gamma$ assembly responses could be used.

Pulses from a NaI(Tl) detector in the neutron assembly were amplified using a gain stabilised amplifier and fed into a Hewlett-Packard 5401B multichannel analyser. Count rates and backgrounds were determined by setting windows in the pulse height spectra. A typical pulse-height spectrum is shown in FIG. 3.

Figure 3:
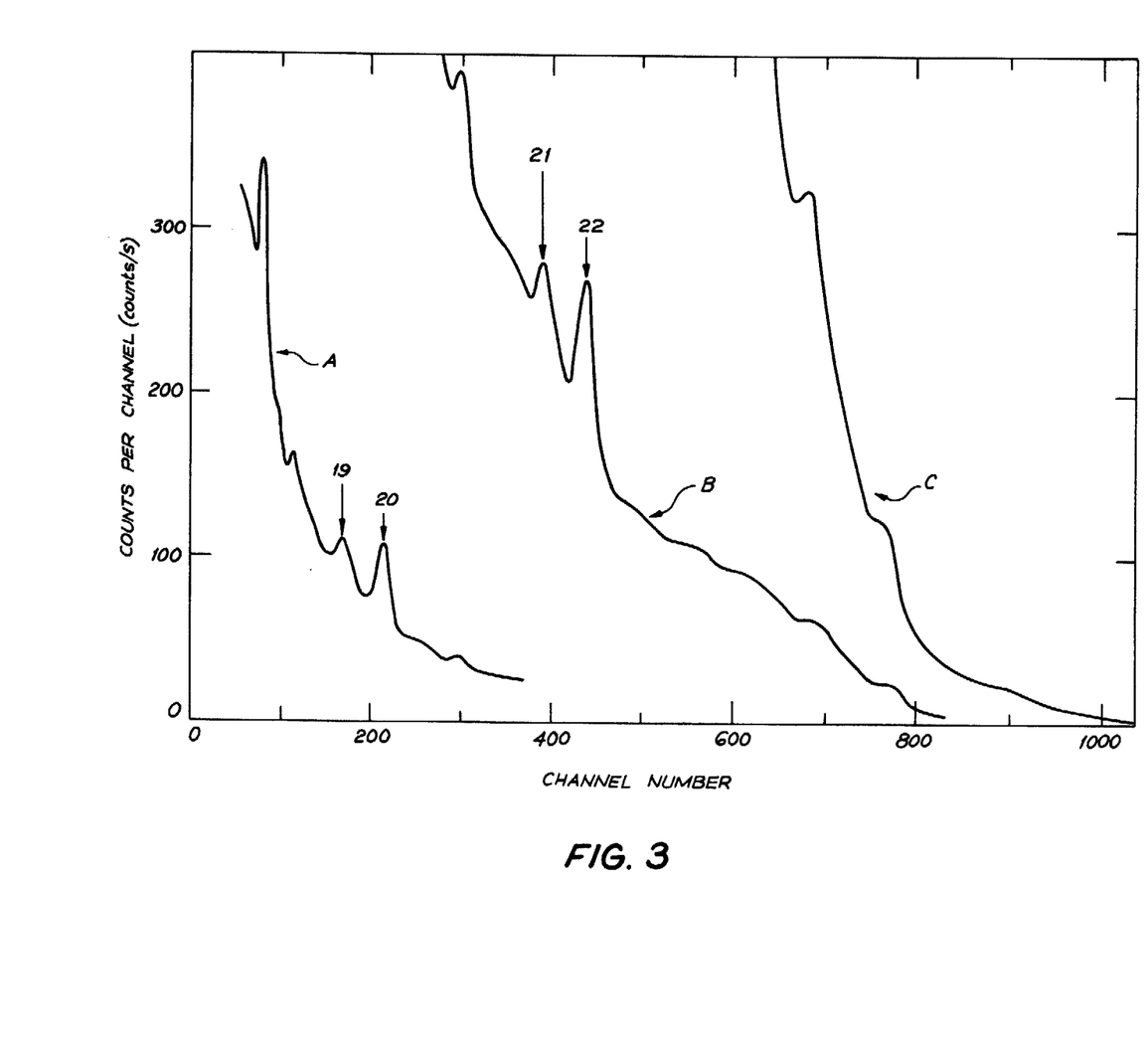
FIG. 3 is a pulse height spectrum obtained using the assembly shown in FIG. 1 with an Australian coal sample containing 76.4 wt % C.

In FIG. 3 curves B and C represent 10 and 50 times magnification, compared with curve A. Peak 19 represents 1.78 MeV Si, 20 represents 2.22 MeV H, 21 represents 3.92 MeV $^{12}$C escape and 22 represents 4.43 MeV $^{12}$C. The 3.92 MeV peak results from the escape of one 0.511 MeV annihilation $\gamma$ ray from the interaction of a 4.43 MeV $^{12}$C $\gamma$ ray in the detector.

Figure 4:
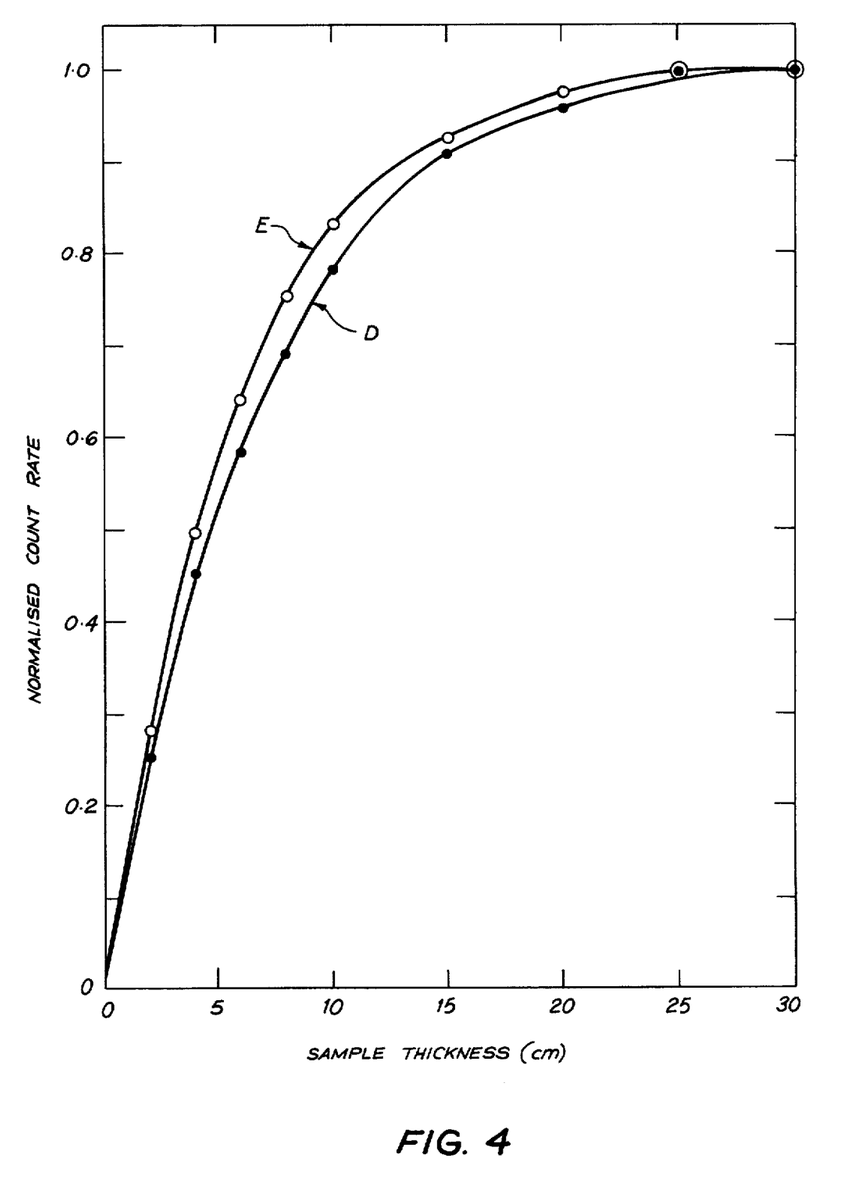
FIG. 4 shows experimental relative count rates as a function of sample thickness for a coal sample on the assemblies shown in FIG. 1 and FIG. 2.

The matching of the response of the two gauges in FIGS. 1 and 2 as a function of sample thickness is shown in FIG. 4. This matching could be further improved by increasing the source to sample distance $d_2$ in FIG. 2 relative to that $d_1$ in FIG. 1.

In FIG. 4 curve D illustrates the 4.43 MeV inelastic $\gamma$ ray yield measured in the assembly illustrated in FIG. 1. Curve E represents the scattered $\gamma$ ray yield measured in the assembly illustrated in FIG. 2.

Coal samples from 44 gallon drums were crushed to $-25$ mm prior to pouring into aluminium containers of dimension 40 cm $\times$ 40 cm $\times$ 30 cm high for analysis. At least 2 sub-samples were analysed as a function of compaction for each of the coal samples tested.

For a typical coal sample the total count rate in the assembly in FIG. 1 was about 70,000 counts/sec ($>250$ keV) and samples were analysed for 10 minutes each. For the $\gamma$ back-scattered assembly the scattered count rate was about 50,000 counts/sec and a counting time of 200 sec per sample was used.

Figure 5:
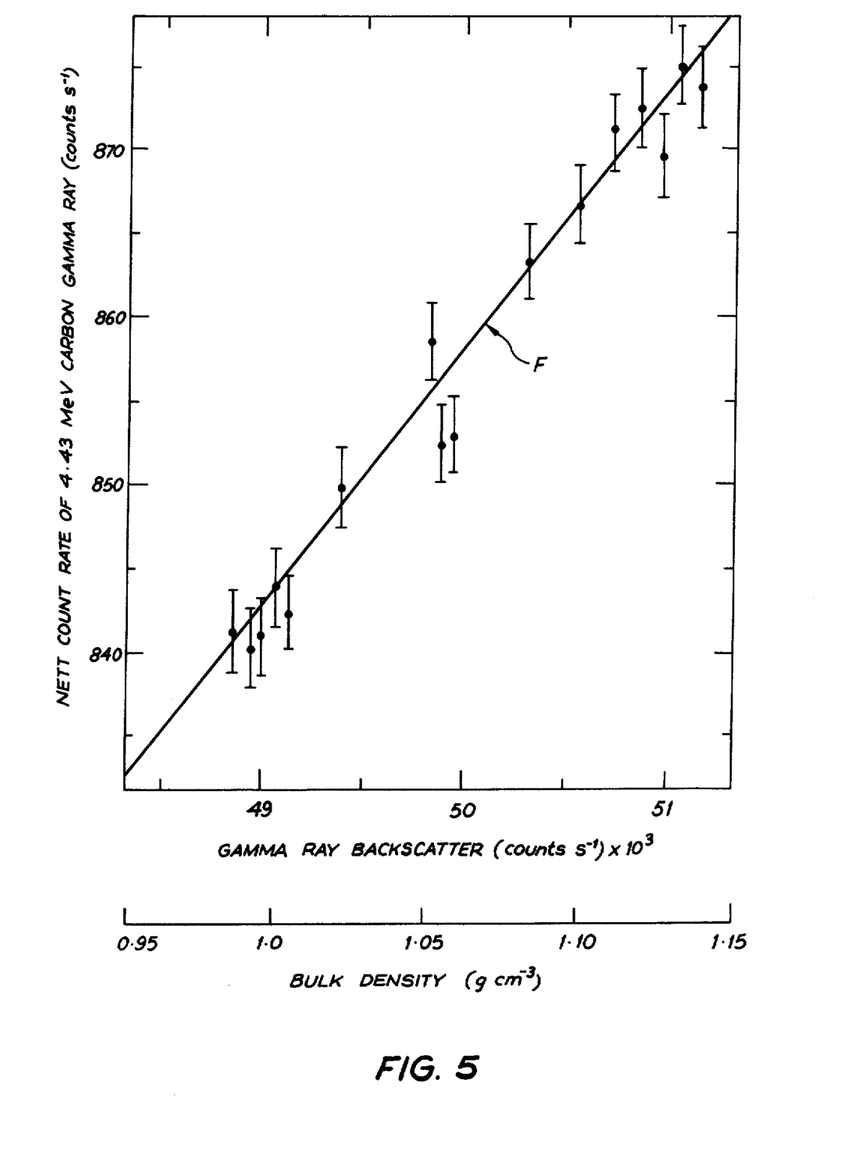
FIG. 5 shows the results of multiple measurements on a single coal sub-sample as a function of compaction.

The results of multiple measurements on a single coal sub-sample as a function of compaction (by shaking, prodding etc.) are shown by curve F in FIG. 5. The data in FIG. 5 cover a bulk density range of about 0.98 to 1.13 g cm$^{-3}$. From FIG. 5 it can be seen that the method of $\gamma$ backscatter compensation can be used to reduce the effects of density variation over this range from 3.5% relative (uncompensated) to less than about 0.3% relative.

The root mean square deviation of the data points about curve F is 3.1 counts/sec which is equivalent to a relative deviation of 0.37% of which 0.29% is due to counting statistics.

Figure 6:
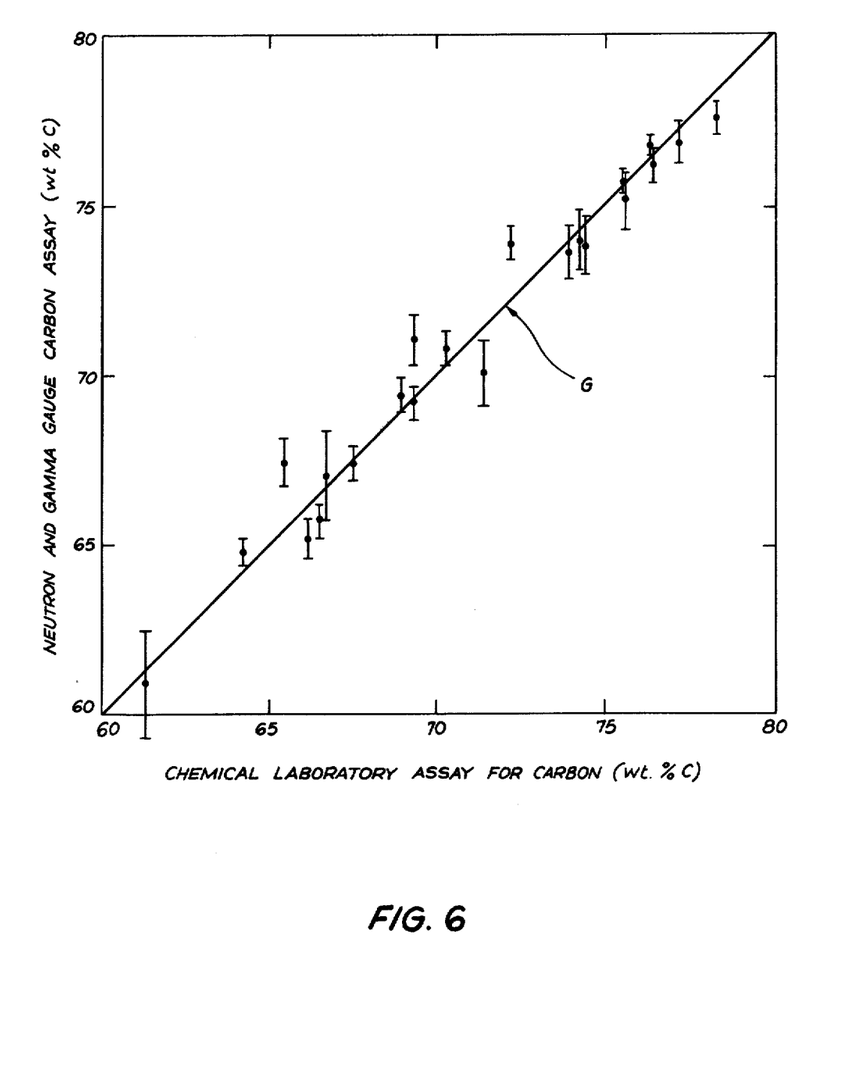
FIG. 6 shows the results of the determination of the carbon content in 22 coal samples from the southern NSW, Australia coalfields.

Results of carbon determination in 22 Australian coal samples are shown as curve G in FIG. 6. Experimental assays based on mean compensated 4.43 MeV count rates for a number of sub-samples are plotted as a function of chemical laboratory assay. Compensated 4.43 MeV count rates are calculated by normalising the neutron inelastic scattering results to a constant $\gamma$ ray scattering count rate using the slope of curve F in FIG. 5. Compensated 4.43 MeV count rates are then essentially independent of sample compaction. The root mean square deviation of the experimental points around the calibration line in FIG. 6 is 0.86 wt % carbon.

Figure 7:
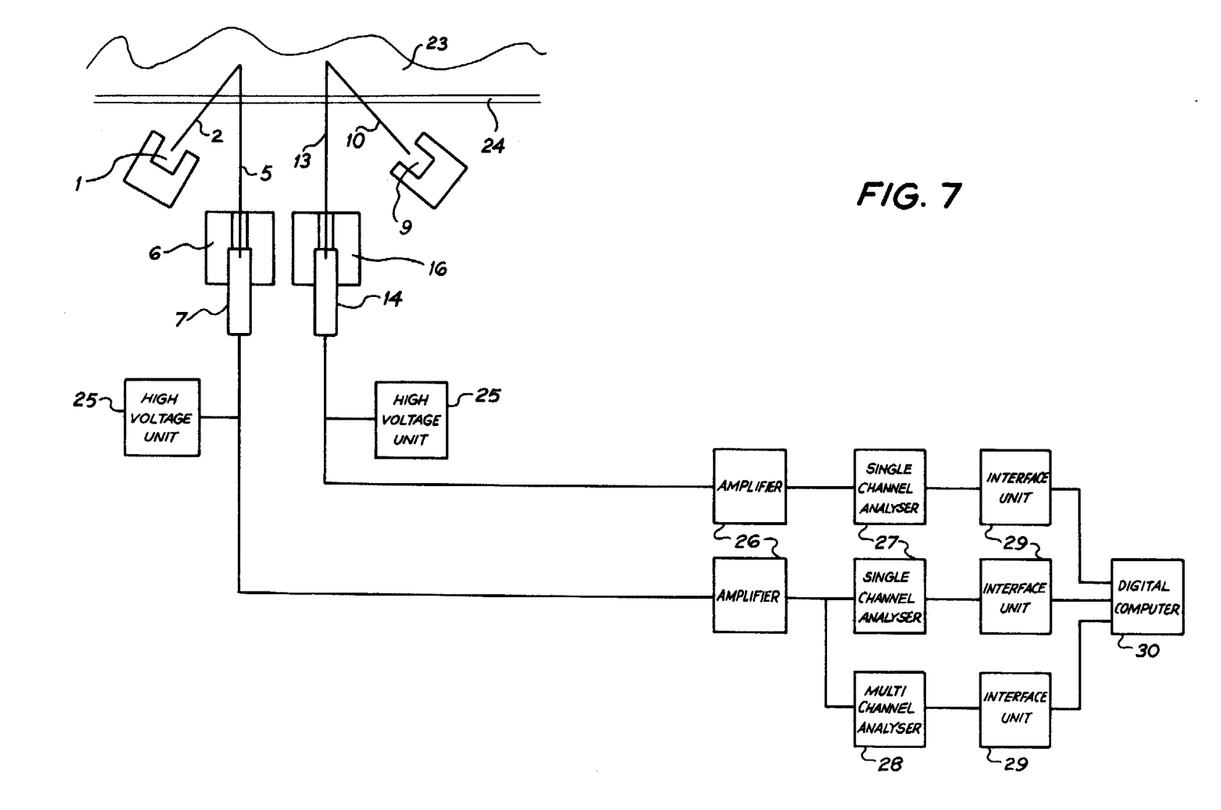
FIG. 7 is a schematic illustration of an apparatus according to the invention.

In FIG. 7 coal 23 on a moving conveyor belt 24 is viewed by a beam 2 of neutrons from source 1 resulting in inelastic scattered $\gamma$ rays 5 which are detected by detector 7 having a shield 6. The coal is also viewed by $\gamma$ rays 10 from source 9 resulting in scattered $\gamma$ rays 13 which are detected by detector 14 having shield 16.

The electronics used with the detectors 7, 14 are known art and comprise high voltage units 25 to operate the detectors 7, 14, amplifiers 26, single channel analysers 27 or multi-channel analyser 28 to select electrical pulse heights corresponding to the appropriate $\gamma$ rays detected, and interface units 29 to link outputs from units 27, 28 with a digital computer 30 which scales the electrical pulses and calculates concentration of the carbon content of coal 23.

Calculations have shown that the specific energy of 110 Australian black coals (Joint Coal Board/Queensland Coal Board, Australian Black Coals, Report, September, 1976) from many different seams can be determined to within 1.6% relative by measuring the carbon content of the coal. On some single seams, specific energy and carbon are correlated to within 0.4% relative.

In practice, three important coal parameters for which on-line analysis is required are specific energy, ash and moisture. The present method can be used to simultaneously determine these three parameters in coal based on a combination of measurement of 4.43 MeV $\gamma$ ray intensity and $\gamma$ ray scattering with a measurement of the intensity of 2.22 MeV hydrogen capture $\gamma$ rays (peak 20 in FIG. 3). This is best explained by considering coal as comprising 3 components, namely coal matter, mineral matter and ash. Coal ash is the oxidised incombustible residue from the combustion of coal, and is closely correlated with the mineral matter content. The determination of carbon as described above closely defines the coal matter component of the coal. As the carbon/hydrogen ratio in coal matter is approximately constant for coal from a particular seam, a hydrogen measurement using the 2.22 MeV hydrogen capture $\gamma$ rays determines moisture and therefore ash by a difference technique. The results of the measurements are summarised in Table 3.

TABLE 3

Summary of results of 81 measurements on 22 Australian coal samples.

| Concentration | Carbon (wt %) | Specific Energy (MJ/kg) | Ash (wt %) | Moisture (wt %) |
|---|---|---|---|---|
| Range | 61.3–78.2 | 25.0–31.9 | 10.2–27.0 | 0.7–14.3 |
| Mean | 71.3 | 29.1 | 14.3 | 4.0 |
| Standard deviation | 4.8 | 2.0 | 5.2 | 4.8 |
| rms deviation* ($\sigma$) | 0.86 | 0.42 | 1.31 | 0.88 |
| $\sigma$/mean (% relative) | 1.2 | 1.4 | 9.2 | 22.0 |

*rms deviation between chemical laboratory assays and assays based on the intensities of 4.43 MeV $\gamma$ rays and $\gamma$ ray backscatter (for carbon and specific energy) or 4.43 and 2.22 MeV $\gamma$ rays and $\gamma$ backscatter (for ash and moisture).

The rms deviations quoted in Table 3 are reduced if less than the full range of 22 samples is considered. For example, if analysis is restricted to samples containing >70 wt % C, rms deviations for carbon, specific energy and ash are 0.41 wt %, 0.28 MJ/kg and 0.83 wt % respectively.

The relatively high rms deviation quoted in Table 3 for moisture is caused by variable ratios of hydrogen and carbon in the coal matter. As coal matter contains about 5 wt % hydrogen and as 1 wt % water contains only 0.11 wt % hydrogen, variations in hydrogen with respect to carbon in the coal matter must be small for accurate moisture measurements. For 20 measurements on one coal sample with added moisture in the range 0.8 to 23.4 wt %, the rms deviation between the experimental and calculated values was only 0.19 wt % water.

Ash can theoretically be determined to within 9% relative error by measuring the compensated intensity of 1.78 MeV silicon inelastic $\gamma$ rays. However in practice rms deviation based on this measurement is 3.8 wt % compared to the value of 1.3 wt % in Table 3. This is partly due to a poor correlation between silicon and ash in the samples tested and partly due to experimental difficulties in accurately measuring the yield of 1.78 MeV $\gamma$ rays.

The results quoted above were obtained with samples which were essentially infinitely thick with respect to the backscatter measurements (FIG. 4). For sample thicknesses less than "infinite," the $\gamma$ ray compensation method will also accurately correct for depth variations provided exact matching of the neutron and $\gamma$ gauges is achieved. In practice this should prove a significant advantage of the method for applications such as on-line conveyor belt analysis.

A geometry suitable for hopper applications could incorporate the source-shield-detector assemblies in a tube in a hopper. The analysis assemblies could be moved to achieve matching. This type of assembly could be used for elemental analysis in boreholes. An alternative arrangement for a hopper application could use sources placed inside the hopper with the detector(s) outside. Another alternative to the backscatter system described above would be to place the sources and detector(s) on opposite sides of a sample and to match the neutron assembly response by a forward scatter or transmission $\gamma$ ray assembly.

Alternative applications could incorporate the neutron and $\gamma$ measurements into one assembly by interchanging sources, provided that acceptable matching of the neutron and $\gamma$ interactions could be obtained. In some cases it may be possible to utilize $\gamma$ rays emitted by the neutron source.

Probably the single most important potential application of the technique is the on-line analysis of coal. Over 80% of Australian black coal is processed in a washing or blending operation before sale or use. Black coal is consumed primarily in the iron and steel industry or in electricity generation. On-line determination of ash and moisture is important in controlling washing and blending operations. Continuous determination of the specific energy of coal to be burned in a power station can provide the means to schedule and optimise the power system load more efficiently. If the specific energy can be measured quickly, it can also result in a greater combustion efficiency by allowing boiler operation at a more nearly optimum fuel-to-air ratio.

Other potential applications include the analysis of carbon in coke, the analysis of aluminium, silicon and iron in bauxite ores, the analysis of iron in iron ores and mineral products and the analysis of silicon in coal.

What I claim is:

1. Measuring apparatus for quantitatively measuring the concentration of an element in a sample containing said element, said apparatus comprising a neutron inelastic scatter assembly, a $\gamma$ ray scatter assembly and means to calculate said concentration from the outputs of said assemblies, said assemblies being matched to measure over essentially the same volume of said sample, said neutron inelastic scatter assembly comprising a first source yielding neutrons having energy sufficient to produce inelastically scattered first $\gamma$ rays from a stable insotope of said element, a first detector to detect said first $\gamma$ rays, and first shield means associated therewith to reduce the intensity of direct source, radiation, said $\gamma$ ray scatter assembly comprising a second source yielding second $\gamma$ rays, a second detector to detect said second $\gamma$ rays scattered from said sample, and second shield means associated therewith to reduce the intensity of direct source $\gamma$ rays.

2. Measuring apparatus as claimed in claim 1 wherein said neutron inelastic scatter assembly and said $\gamma$ ray scatter assembly are located on the same side of said sample.

3. Measuring apparatus as claimed in claim 1 wherein said first source is located on the opposite side of said sample to said first detector.

4. Measuring apparatus as claimed in claim 3 wherein said second source is located on the opposite side of said sample to said second detector.

5. Measuring apparatus as claimed in claim 1 wherein said second source is located on the opposite side of said sample to said second detector.

6. Measuring apparatus as claimed in claim 1 wherein said first and second detectors are replaced by a single detector and measurement is achieved by interchange of said first and second sources.

7. Measuring apparatus as claimed in claim 1 wherein said first and second sources are replaced by a single source yielding said second $\gamma$ rays and neutrons of energy sufficient to produce said first $\gamma$ rays, and said first and second detectors are replaced by a single detector, measurement being achieved by separating the detection of $\gamma$ rays from said neutron inelastic scatter and said scattered second $\gamma$ rays by pulse height analysis.

8. Measuring apparatus as claimed in claim 1 adapted to measure carbon content and specific energy of coal or coke by 4.43 MeV carbon $\gamma$ rays, wherein said first source yields neutrons having energy sufficient to produce inelastically scattered 4.43 MeV carbon $\gamma$ rays.

9. Measuring apparatus as claimed in claim 8 adapted to measure one or more of moisture, ash or hydrogen content of coal or coke, wherein said first source also yields neutrons which produce 2.2 MeV hydrogen capture $\gamma$ rays.

10. Measuring apparatus as claimed in claim 1 further comprising one or more measuring means which measure 2.2 MeV hydrogen capture $\gamma$ rays, thermal neutron flux, epithermal neutron flux, capacitance or infra-red reflectance, to apply a correction for moisture content of said sample.

11. A method for quantitatively measuring one or more elements in a sample, said method comprising combining the results of (i) a measurement of neutron inelastic scatter $\gamma$ rays over a selected volume of said sample, and (ii) a measurement of $\gamma$ ray scatter over said selected volume.

12. The method as claimed in claim 11 further comprising combining the result of (iii) the measurement of one or more of 2.2 MeV hydrogen capture $\gamma$ rays, thermal neutron flux, epithermal neutron flux, capacitance, or infra-red reflectance.

13. The method as claimed in claim 11 wherein said sample is coal or coke and said element is carbon and wherein the measurement is used to determine the specific energy of said coal or coke by 4.43 MeV carbon neutron inelastic scatter $\gamma$ rays.

14. The method as claimed in claim 13 further comprising measurement of one or more of moisutre, ash or hydrogen content by detection of 2.2 MeV hydrogen capture $\gamma$ rays.

* * * * *